United States Patent [19]
Boender

[11] Patent Number: 6,106,560
[45] Date of Patent: Aug. 22, 2000

[54] HYDRAULIC KNEE JOINT

[75] Inventor: Jacob Quintus Laurens Anthony Boender, Marcham, United Kingdom

[73] Assignee: Michael O'Byrne, Oxford, United Kingdom

[21] Appl. No.: 09/281,338

[22] Filed: Mar. 30, 1999

[51] Int. Cl.[7] .................................................. A61F 2/64
[52] U.S. Cl. ........................................... 623/44; 623/43
[58] Field of Search .......................................... 623/39–45

[56] References Cited

U.S. PATENT DOCUMENTS

| | | |
|---|---|---|
| 4,662,486 | 5/1987 | Stenberg . |
| 4,775,037 | 10/1988 | Stenberg . |
| 5,376,136 | 12/1994 | Stenberg . |

FOREIGN PATENT DOCUMENTS

| | | |
|---|---|---|
| 8500740 | 5/1989 | Sweden . |
| 1380428 | 1/1975 | United Kingdom . |

*Primary Examiner*—Bruce Snow
*Attorney, Agent, or Firm*—McEachran, Jambor, Keating, Bock & Kurtz

[57] ABSTRACT

A patient-weight-activated hydraulic knee joint in which flow between hydraulic chambers is controlled by a valve operated by hydraulic pressure and by a force transmission system which transmits the force of a patient's weight, such that the valve is only closed when the patient's weight acts on the knee joint. Closure of the valve locks the knee joint, so hence undesirable locking does not occur during the swing phase of the patient's gait. A damped hydraulic trip valve can also be provided to give improved operation of the knee joint.

16 Claims, 4 Drawing Sheets

HYDRAULIC KNEE JOINT

BACKGROUND OF THE INVENTION

The present invention relates to a hydraulic knee joint.

Persons requiring an above-knee amputation lose both their knee and the remainder of the leg below the knee. An external prosthesis can serve to replace the lost function of the knee and foot. Modern prostheses are often modular in function, such that the knee and foot prostheses are separate units which work together to form an artificial limb. It is desirable for any artificial foot to be able to function in combination with any artificial knee joint. Thus an artificial knee joint should ideally provide for this modular function.

In use, an artificial knee joint must typically perform a stability function to provide stability when the user (patient) is standing and requiring the artificial limb to bear their weight or when the artificial limb is bearing weight during walking (stance phase), and must also be able to flex freely during the swing phase of the patient's gait.

Previously proposed artificial knee joints can be broadly classified as those providing stability via geometric stability, static friction stability or hydraulic stability. Control of the swing phase can be based on the use of springs, dynamic friction, pneumatic fluid resistance, hydraulic fluid, or hysteresis in solids.

The Regnell limb is an example of a hydraulic swing and stance controlled artificial knee, which is controlled by the position of the foot. It uses a cylinder piston arrangement, as described in SE 8,500,740-9, U.S. Pat. No. 4,662,486 and U.S. Pat. No. 4,775,037, in which the below-knee section of the artificial limb comprises an upper and a lower hydraulic chamber, each having a piston held on a common piston rod, arid the piston being pivotally connected to the artificial knee joint. If the flow of hydraulic fluid between the chambers is blocked, the knee joint is prevented from bending and the limb is locked in position. This can provide the required stability function so that the leg is locked in a substantially straight position during weight bearing. A control valve governing the flow between the hydraulic chambers to provide switching between hydraulic swing control and hydraulic stance control is proposed in GB-A-1380428. The control is provided by the position of the foot, an arrangement which requires a specific prosthetic foot to be used in conjunction with a specific prosthetic leg.

In line with modern requirements, attempts have been made to develop the Regnell limb into a modular system. U.S. Pat. No. 5,376,136 discloses a means of control of the hydraulic valve in the piston arrangement to provide modular function whereby the below-knee section comprises two hinged parts, the relative positions of which control the valve. Thus control is provided by the leg section alone, and not the foot, so that modularisation is achieved. However, the device has proved to be cumbersome, unreliable and subject to wear. In addition, when in use, the inertia of the foot and shoe during swing can result in motion of the below-knee section such as to cause locking of the knee joint into the stance mode necessary to support the patient when standing. This is clearly disadvantageous as the patient is thus prevented from taking further steps. Thus systems which rely on the position of parts of the artificial limb have generally proved unsatisfactory.

The so-called Catranis system is an alternative attempt to control the switching between stance and swing. It utilises an offset lever system to operate a valve arrangement. However, it too suffers from tendency to locking. The resistance of the hydraulic unit in motion during the swing phase produces a similar force pattern on the lever system to that produced by the application of the patient's weight when standing, with the result that the knee locks into the stance position during the swing phase.

Typically, the ratio of the forces generated in an artificial knee joint during swing phase and during stance phase is of the order of 1:5. The above mentioned systems fail to produce adequate control because during swing phase they are subject the large forces arising from the inertia of the foot and lower parts of the prosthesis.

An aim of the present invention is to address this disadvantage.

Accordingly a first aspect of the present invention is directed to a patient-weight-activated hydraulic knee joint comprising a hydraulic shaft system comprising a cylinder having an upper chamber and a lower chamber divided by a partition, a piston disposed within each chamber and dividing each chamber into a lower section and an upper section, a piston rod joining the pistons and passing through the partition, a first hydraulic line connecting the upper section of the upper hydraulic chamber and the lower section of the lower hydraulic chamber, and a second hydraulic line connecting the lower section of the upper chamber and the upper section of the lower chamber, and further comprising a frame holding the hydraulic shaft system, a knee attachment pivotally mounted on the frame, a crank shaft disposed within the knee attachment and having a pivot axis, a pivot pin disposed within the knee attachment with an axis parallel to that of the crank shaft to which the piston rod is pivotally connected and thereby transmits hydraulic force, force transmission means are connected to the crank shaft which transmit the force of a patient's weight when brought to bear on the knee attachment, in which a hydraulic valve is situated in the second hydraulic line and controlled by the force transmission system and hydraulic pressure such that combined application of the patient's weight via the force transmission system and the hydraulic pressure to the valve stops the flow of hydraulic fluid. This is advantageous in that control depends on application of the patient's weight so that locking occurs only when it is required, that is, during standing and those parts of the patient's gait when the limb is weight-bearing. Furthermore, the control is provided solely by features of the hydraulic knee joint, thus providing a fully modular unit.

Preferably, the cylinder is adapted at its lower end for attachment to a prosthetic ankle and foot.

Preferably, the knee attachment is adapted for attachment via suitable connectors to a leg stump.

Advantageously, auxiliary controls are provided to pre-set the level of patient weight required for the hydraulic valve to close during weight-bearing. Thus the hydraulic knee joint can be readily altered to suit the characteristics of a patient.

Preferably, the force transmission system comprises a lever system pivotally connected to the knee attachment at one end and at the other end to the valve.

Advantageously the lever system comprises a long lever pivotally fastened at one end to the crank shaft, a chain link pivotally fastened to the other end of the long lever, and a short lever pivotally fastened to the chain link. This provides an effective and straightforward way of transmitting the forces from the knee attachment to the valve.

Preferably, low friction means are provided to transfer the force of the patient's weight to the force transmission means. This allows efficient transfer of the force.

Advantageously the low friction means are roller bearings.

In a preferred embodiment the short lever controls the position of the hydraulic valve. This arrangement minimises the number of components of the force transmission system.

Advantageously, the movement of the short lever is constrained by auxiliary controls. Thus the movement required to operate the valve effectively can be adjusted if necessary.

Preferably, the pivot axis of the crank shaft is eccentric.

In a preferred embodiment the pivot pin axis is situated forwardly and downwardly of the crank shaft axis.

Advantageously, the eccentric pivot axis of the crank shaft and the pivot point of the knee attachment about the frame lie within a plane also containing a point in front of a patient's foot when the patient is using the patient-weight-activated hydraulic knee joint and standing upright. This arrangement reduces the tendency of hydraulic knee joint to lock into stance phase when the weight of the patient passes through the toe of the foot as compared to the heel of the foot.

In a preferred embodiment, the hydraulic valve comprises a hydraulic chamber containing a rotary shaft controlled by the force transmission system, and a piston moved by the rotary shaft.

Advantageously the hydraulic valve further comprises a valve seat which may be substantially sealed by the piston to close the second hydraulic line, the area of the piston being much greater than the area of the valve seat. This greater area provides a simple way of maintaining sufficient force during motion to keep the valve open and hence prevent the knee joint from locking.

Advantageously the hydraulic valve further comprises a passage leading from the chamber to the hydraulic line and containing a needle valve. This regulates the hydraulic flow.

Advantageously, the rotary shaft co-operates with a slot in the aide of the piston to effect movement of the piston. This provides a simple, low friction way of moving the piston.

Preferably the knee attachment comprises a substantially ball-like member.

A second aspect of the present invention is directed to a hydraulic trip valve for use in a hydraulic prosthetic joint comprising a flow passage between two hydraulic chambers and containing therein a first valve, a flow restrictor and a second valve which opens at a predetermined hydraulic pressure. The trip valve offers the advantage that flow through the flow passage can be prevented when the hydraulic pressure is below a predetermined level.

Advantageously the hydraulic trip valve is further provided with a damping member. This prevents the second valve from closing too quickly and thus reduces resonance effects.

Advantageously the second valve comprises a hydraulically damped piston.

Preferably the hydraulically damped piston is provided with a pressure relief ball valve which cooperates with the valve seat.

Advantageously the hydraulically damped piston is mounted on a spring having a spring force (S) which urges the valve to a closed position against a valve seat of area (A3).

In a preferred embodiment the spring force (S) and the valve seat area (A3) are predetermined according to P=S/A3 where P is the hydraulic pressure acting to open the valve arising from the gravitational forces acting when the joint is substantially at rest, Thus the parameters S and A3 can be selected to tailor the operation of the trip valve to the individual characteristics of the patient, Preferably the flow restrictor comprises a needle valve. In this way the flow through the flow passage can be at a different rate in either direction.

Advantageously the damping member comprises a constriction in the flow passage.

Preferably the damping member is situated in a flow passage acting in parallel with the flow restrictor.

Preferably, the hydraulic trip valve further comprises a bypass valve which bypasses the valve seat. This allows the operation of the trip valve to be adjusted to balance the operation of the needle valve.

Advantageously, the patient-weight-activated hydraulic knee joint disclosed above further comprises such a hydraulic trip valve.

BRIEF DESCRIPTION OF THE DRAWINGS

An example of a hydraulic knee joint made in accordance with the present invention will now be described with reference to the accompanying drawings, in which.

DETAILED DESCRIPTION OF THE INVENTION

Figure 1:
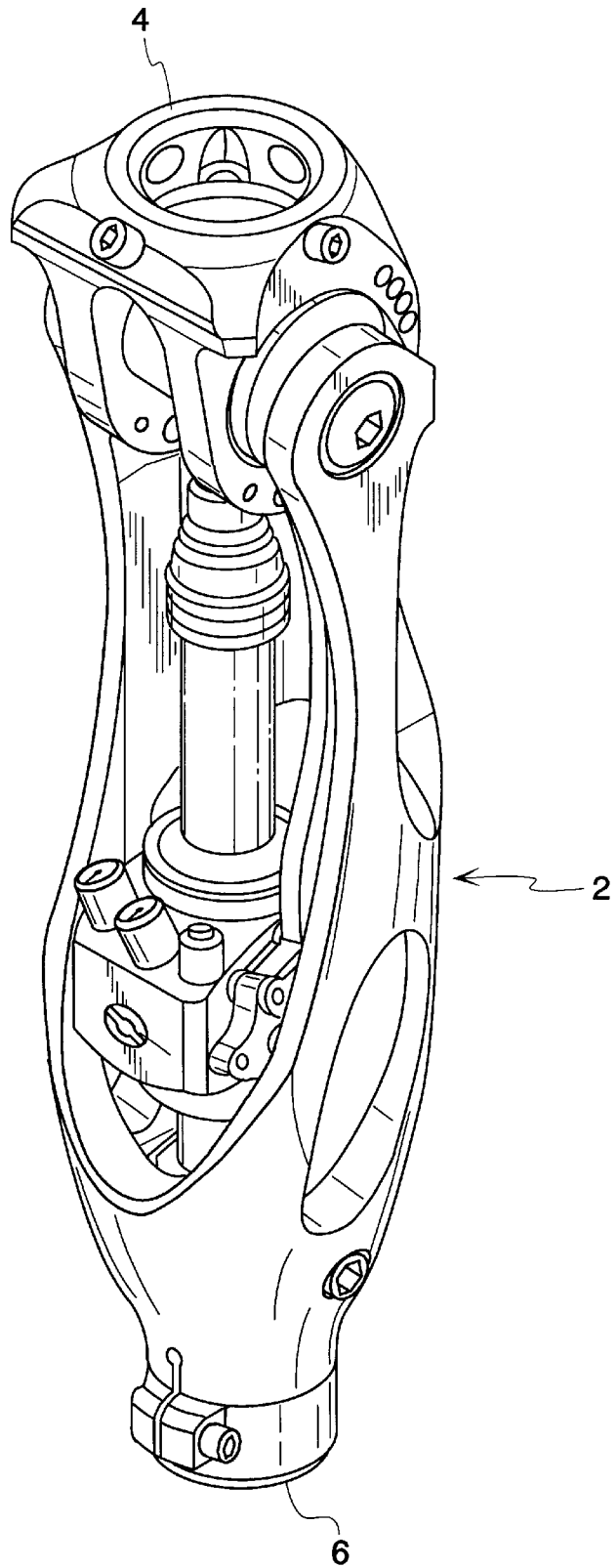
FIG. 1 shows a perspective view from the rear and to one side of such a knee joint.

FIG. 1 shows a hydraulic knee joint 2 adapted at its upper end 4 to be fitted to an amputee's upper leg, and adapted at its lower end 6 to be fitted to a prosthetic ankle and foot.

Figure 2:
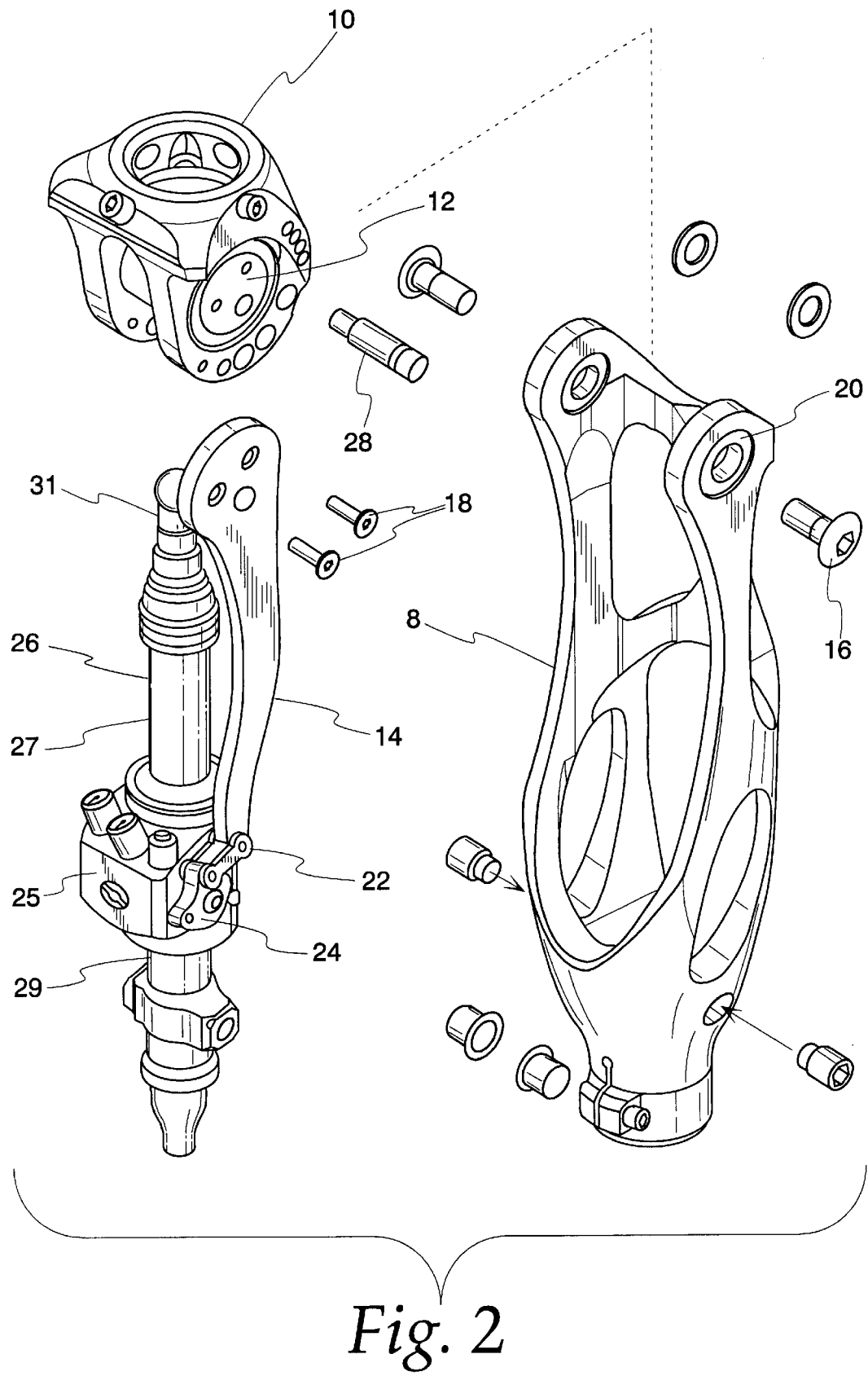
FIG. 2 shows an exploded view of the knee joint of FIG. 1.

The components of the hydraulic knee joint 2 are shown in FIG. 2. A knee ball 10 is hingedly fastened to a frame a. The knee ball 10 is equipped with a crank shaft 12, to which is attached by screws 18 to one end of a long lever 14. The axis of the crank shaft 12 is the pivot axis of the knee joint. Further screws 16 are pivotally attached to the frame a through roller bearings 20, pass through the long lever 14 and engage eccentrically in the crank shaft 12 of the knee ball 10, movably securing the frame 8 thereto. The knee ball 10 is further provided with low friction means (not shown) to transfer forces to the crank shaft 12.

The other end of the long lever 14 is pivotally attached to a chain link 22, which is itself pivotally attached to a short lever 24. The short lever 24 operates a hydraulic valve 30 situated within a housing 25.

A hydraulic shaft 26 (FIG. 3), preferably being a system as disclosed in SE 8500740-9, U.S. Pat. No. 4,662,486 and U.S. Pat. No. 4,775,037, is disposed below the knee ball 10. The hydraulic shaft 26 comprises a cylinder 17 forming an upper hydraulic chamber 27 and a lower hydraulic chamber 29. Each chamber is provided with a piston 23, the two pistons 23 being connected to a common piston rod 31 passing through a partition 15 separating the upper chamber 27 from the lower chamber 29. The pistons 23 thus divide each chamber 27, 29 into a lower section and an upper section. A first hydraulic line 21 connects the upper section of the upper chamber 27 to the lower section of the lower chamber 29. A second hydraulic line 19 connects the lower section of the upper chamber 27 to the upper section of the lower chamber 29. This line 19 is provided with the hydraulic valve 30 contained within the housing 25. The hydraulic shaft 26 is adapted at its lower end for attachment to an artificial ankle and foot (not shown) The upper end of the piston rod 31 is connected to the knee ball 10 via a pivot pin 28 having its axis of rotation parallel to the pivot axis of the knee joint defined by the crank shaft 12, and situated forwardly and downwardly thereof. Thus, bending of the knee about the pivot axis pulls on the pistons via the piston rod 31 so that the lower section of the upper hydraulic chamber 27 increases in volume and the upper section of the lower hydraulic chamber 29 decreases in volume.

Figure 4:
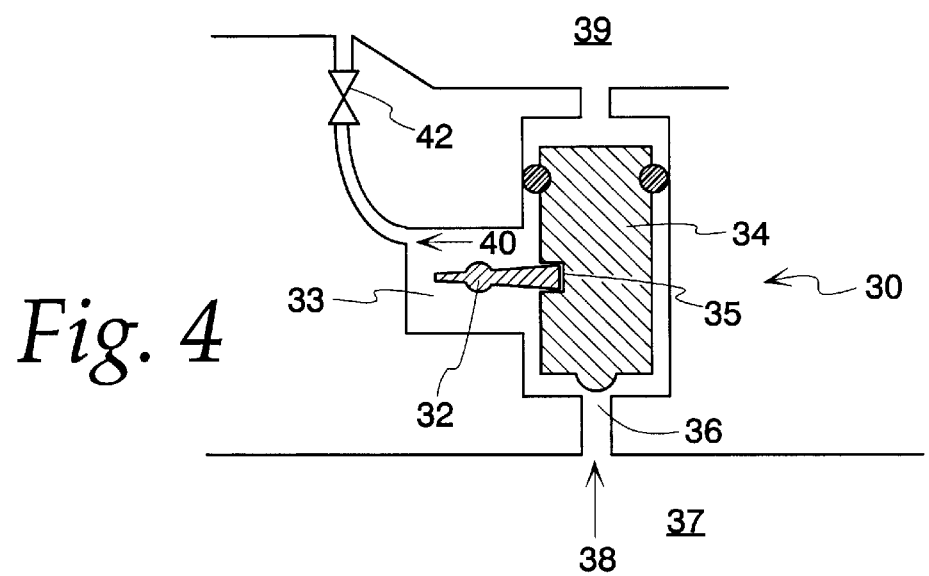
FIG. 4 shows a sectional schematic view of a hydraulic valve fitted within the knee joint.

FIG. 4 shows the internal construction of the hydraulic valve 30 disposed within the housing 25 and situated in the hydraulic line connecting the upper section 37 of the lower hydraulic chamber 29 to the lower section 39 of the upper hydraulic chamber 27. The components of the valve 30 are contained within an oil-filled chamber 33 connected via passages to the hydraulic line.

The short lever 24 is connected through the wall of the housing 25 to a rotary shaft 32. The end portion of the rotary shaft 32 is disposed within a slot 35 in the side of a piston 34. One end of the piston is adapted to co-operate with a valve seat 36 and hence to close a passage leading to the upper part 37 of the lower hydraulic chamber 29. A further passage is arranged to lead from the main chamber 33 in the vicinity of the rotary shaft 32 to the lower section 39 of the upper hydraulic chamber 27. This passage is fitted with a needle valve 42.

The valve seat 36 has an area A1, and the piston 34 has an area A2, such that A2>>A1.

Figure 3:
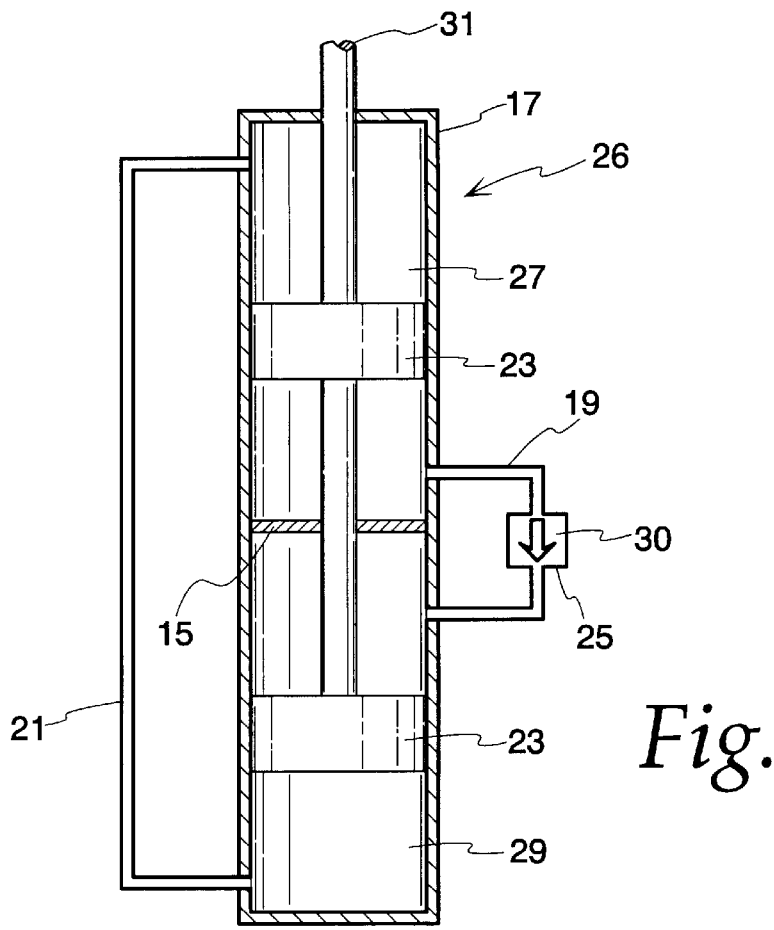
FIG. 3 shows a sectional schematic view of a hydraulic shaft fitted within the knee joint.

The operation and locking of the hydraulic knee joint 2 illustrated in FIGS. 1, 2 and 3 is controlled by the weight of the patient to whom the joint is fitted. In use, the knee joint operates as described herein below:

When the patient applies his weight to the knee joint 2, for example when standing, or during heel strike of his gait, when the leg is extended, this force bears on the knee ball 10, and low friction means transfer part of this force to the crank shaft 12. The force passes via the long lever 14 and the chain link 22 to the short lever 24. The short lever 24 has its motion constrained by auxiliary controls (not shown). The resultant motion of the short lever 24 drives the rotary shaft 32 which in turn moves the piston 34 in such a way as to bring it into contact with the valve seat 36, thus closing the passage. In response to this, the oil exerts a reaction force on the piston 34 via the hydraulic pressure P1 38 in the upper section 37 of the lower hydraulic chamber 29. Thus the hydraulic line between the upper section 37 of the lower hydraulic chamber 29 and the lower section 39 of the upper hydraulic chamber 27 is closed, preventing fluid flow so that the pistons cannot move. Thus the leg is locked in extended position.

Whilst the patient's weight remains applied to the knee joint 2, the action of the hydraulic shaft 26 is to cause resistance against bending of the knee joint 2 about the axis 12 by pulling on pivot pin 28, thus maintaining the leg in a straight position. This operation of the hydraulic shaft 26 causes a similar pattern of force on the knee ball 10 as that produced by the patient's weight acting directly. Thus force is transferred to the valve 30 via the long lever 14, chain link 22, short lever 24 and rotary shaft 32 (comprising together a crank-lever system), further acting to keep the valve 30 closed, and the knee joint locked.

When the patient's weight is removed from the knee joint 2, during walking, for example, the forces acting through the knee ball 10 and the crank-lever system to the valve 30 are removed, and the valve 30 opens. The hydraulic pressure P1 now acts on the larger area A2 of the piston 34. Given that Force=Pressure×Area, the force F2 acting on the piston area A2 is thus greater than the force F1 previously acting on the valve in the closed position when P1 acted on A1 only. As the limb is swung during the taking of a step, any hydraulic resistance forces produced by the hydraulic shaft 26 and transferred via the knee ball 10 and the crank-lever system to the valve 30 are insufficient to overcome F1 and close the valve 30, in the absence of the additional force transferred from the patient's weight when the knee is weight-bearing. Thus the valve 30 remains open during swing phase, fluid can pass along the hydraulic line between the upper section 37 of the lower hydraulic chamber 29 and the lower section 39 of the upper hydraulic chamber 27, the pistons are free to move and the knee joint is prevented from locking.

Auxiliary controls may be: provided to pre-set the amount of patient weight required for the valve 30 to close during weight bearing. Thus the hydraulic knee joint 2 can be tailored to the requirements of a particular patient.

Hydraulic flow through the hydraulic line when the valve 30 is open is regulated by means of a needle valve 42 situated within a passage leading from the main chamber containing the piston 34, The needle valve regulates oil flow between chambers in accordance with SE 8500740-9, U.S. Pat. No. 4,662,486 and U.S. Pat. No. 4,775,037. Furthermore, when the valve 30 is closed by the piston 34 being brought to bear on the valve seat 36, the pressure drop behind the valve seat 36 is secured through the needle valve 42. The pressure drop is given by P1–P2, where P1 is the pressure 38 bearing, on the closed valve at valve seat 36, having area A1, and P2 is the pressure 40 bearing on the passage containing the needle valve 42.

When the valve 30 is opened, the pressure drop is limited by the needle valve 42 and by oil flow through the valve seat 36. This secures full pressure on the piston 34 having area A2, which acts to maintain the valve 30 in the open position, and to keep the knee joint unlocked.

Figure 5:
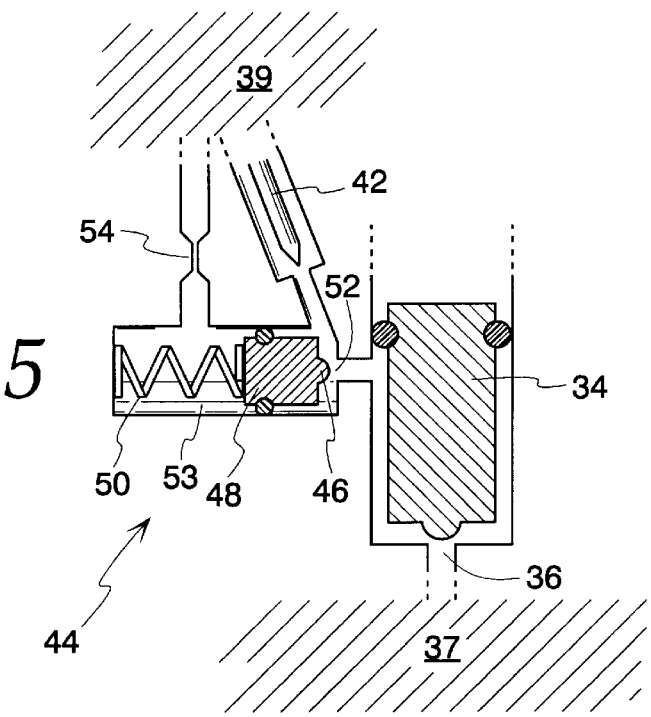
FIG. 5 shows a sectional schematic view of a hydraulic trip valve fitted within the knee joint.

A further embodiment of the valve 30 is shown in FIG. 5. The valve arrangement of FIG. 4 is further provided with a trip valve 44. The passage leading to the needle valve 42 and hence to the lower part 39 of the upper hydraulic chamber 27 is provided with a valve seat 52, leading to a chamber 53, The valve seat 52 has an area A3, The needle valve 42 is situated such that the oil flow through the needle valve 42 and hydraulic line may be blocked by a pressure relief ball valve 46 sealing the valve seat 52. The ball valve 46 is mounted on a piston 48 which is constrained to move back and forth within the chamber 53. The piston 48 is hydraulically damped by a spring 50 having a spring force S.

The chamber 53 is further provided with a passage, having a constriction 54, which leads from the chamber 53 at a point to the rear of the piston 48, to the lower section 39 of the upper hydraulic chamber 27

The hydraulic pressure, P3, which can be held by the trip valve 44 is given by P3=S/A3. During use, the trip valve 44 is required to hold a pressure (and hence keep the hydraulic line closed) which is related to the gravitational force acting at between 60 degrees and 90 degrees relative to the shin section of the artificial limb. Hence, S and A3 are chosen appropriately to balance this, and will depend on the characteristics of the patient, During walking, or movement of the leg, in conjunction with inertia effects, pressures exceeding P3 are produced. This excess pressure bears on the ball valve 46, the piston 48 is forced away from the valve seat 52 and the trip valve 44 opens. The passage to the needle valve 42 is thus opened and the needle valve 42 controls the flow of oil between the upper section 37 of the lower hydraulic chamber 29 and the lower section 39 of the upper hydraulic chamber 27, and the knee joint is maintained in an unlocked configuration during the movement.

As the patient walks, on the terminal phase of the flexion stroke of his gait, the angular velocity of the limb approaches zero, so that the pressure acting on the ball valve 46 is reduced. The ball valve 46 is thus able to close. however, the effect of the constriction 54 is a damping one, and prevents the ball valve 46 from closing too quickly. Hence resonance effects are avoided. The delay in the ball valve 46 closure caused by the constriction 54 is such as to only allow full closure of the valve 30 land hence locking of the knee joint, during the extension stroke of the gait, ready for the next swing phase, and not during the flexion stroke.

The arrangement of the ball valve 46 and piston 48 helps to maintain the pressure on valve seat 36 and piston 34. In addition, oil may flow between the upper section 37 of the lower hydraulic chamber 29 and the lower section 39 of the upper hydraulic chamber 27 only at a pre-determined and controlled level of knee movement, as determined by spring force S and area A3. This feature can operate to facilitate the holding ability of the limb such that the knee joint can remain locked rigid in a desired position against gravitational pull when, for example, the patient wants to lift the limb into a car or over an obstacle.

Additionally, a bypass valve which bypasses the valve seat 52 can be provided which enables the operation of the trip valve 44 to be adjusted to balance the operation of the needle valve 42. This removes any requirement for strong extension assists in the hydraulic knee joint 2.

Figure 6:
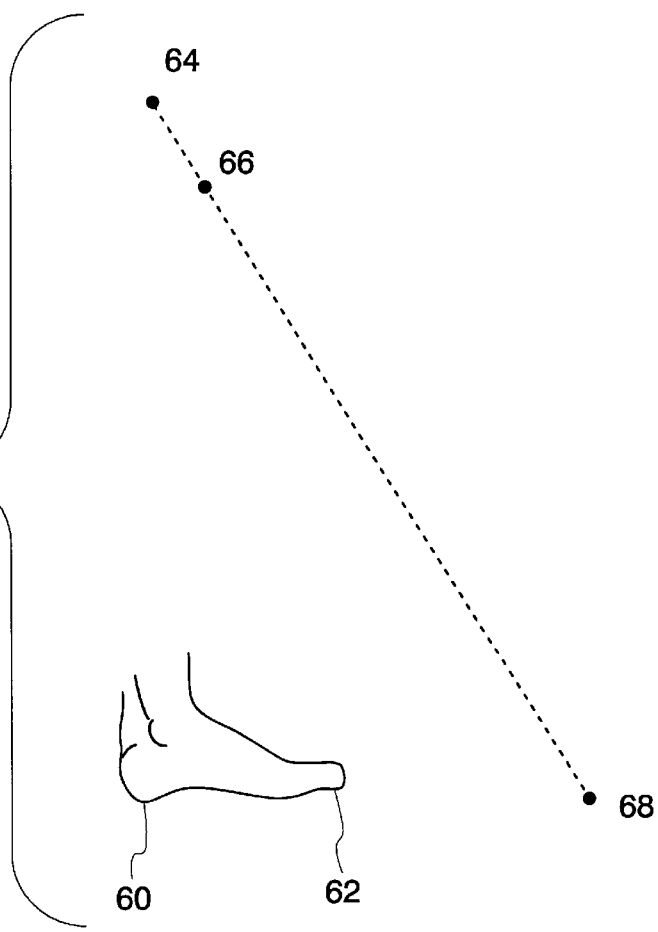
FIG. 6 shows the relative position of some parts of the knee joint in use.

FIG. 6 illustrates an advantageous arrangement of the components of the hydraulic knee joint 12 when in use. The knee joint contains, especially, two pivot points defined by the knee joint pivot axis 64 of the crank shaft 12, and the pivot axis 66 defined by the screws is. These axes are arranged such that when the artificial knee Joint is in use and the patient is standing upright, the pivot Iaxis 66 is positioned below and forward of the pivot axis 64, both points being situated substantially over the patient's foot. Further, these pivot axes lie in a plane also containing a point 68 in front of the foot. This arrangement results in a reduced tendency of the crank-lever system to engage control of the stance phase of the knee, that is, locking of the joint derived from the closure of the valve 30, when the weight of the patient passes through the toe 62 of the foot as compared to the weight passing through the heel 60 of the foot. Thus locking of the knee joint is produced at heel strike as desired, and the joint will begin to unlock as the "toe off" phase of the gait is approached. This benefit arises because the geometry results in a reduced efficiency of the crank-lever system in relation to the direction of the ground reaction force.

What is claimed is:

1. A patient-weight-activated hydraulic knee joint comprising a hydraulic shaft system comprising a cylinder having an upper chamber and a lower chamber divided by a partition, a piston disposed within each chamber and dividing each chamber into a lower section and an upper section, a piston rod joining the pistons and passing through the partition, a first hydraulic line connecting the upper section of the upper hydraulic chamber and the lower section of the lower hydraulic chamber, and a second hydraulic line connecting the lower section of the upper chamber and the upper section of the lower chamber, and further comprising a frame holding the hydraulic shaft system, a knee attachment pivotally mounted on the frame, a crank shaft disposed within the knee attachment and having a pivot axis, a pivot pin disposed within the knee attachment with an axis parallel to that of the crank shaft to which the piston rod is pivotally connected and thereby transmits hydraulic force, force transmission means are connected to the crank shaft which transmit the force of a patient's weight when brought to bear on the knee attachment, in which a hydraulic valve is situated in the second hydraulic line and controlled by the force transmission means and hydraulic pressure such that combined application of the patient's weight via the force transmission means and the hydraulic pressure to the valve stops the flow of hydraulic fluid.

2. A patient-weight-activated hydraulic knee joint according to claim 1 in which the cylinder is adapted at its lower end for attachment to a prosthetic ankle and foot.

3. A patient-weight-activated hydraulic knee joint according to claim 1, in which the knee attachment is adapted for attachment via suitable connectors to a leg stump.

4. A patient-weight-activated hydraulic knee joint according to claim 1, in which the force transmission system comprises a lever system pivotally connected to the knee attachment at one end and at the other end to the valve.

5. A patient-weight-activated hydraulic knee joint according to claim 4, in which the lever system comprises a long lever pivotally fastened at one end to the crank shaft, a chain link pivotally fastened to the other end of the long lever, and a short lever pivotally fastened to the chain link.

6. A patient-weight-activated hydraulic knee joint according to claim 5, in which the short lever controls the position of the hydraulic valve.

7. A patient-weight-activated hydraulic knee joint according to claim 1, in which low friction means are provided to transfer the force of the patient's weight to the force transmission means.

8. A patient-weight-activated hydraulic knee joint according to claim 7, in which the low friction means are roller bearings.

9. A patient-weight-activated hydraulic knee joint according to claim 1, in which the pivot axis lot the crank shaft is eccentric.

10. A patient-weight-activated hydraulic knee joint according to claim 1, in which the pivot pin axis is situated forwardly and downwardly of the crank shaft axis.

11. A patient-weight-activated hydraulic knee joint according to claim 1, in which the pivot axis of the crank shaft and the pivot point of the knee attachment about the frame lie within a plane also containing a point in front of a patient's foot when the patient is using the patient-weight-activated hydraulic knee joint and standing upright.

12. A patient-weight-activated hydraulic knee joint according to claim 1, in which the hydraulic valve comprises a hydraulic chamber containing a rotary shaft controlled by the force transmission system, and a piston moved by the rotary shaft.

13. A patient-weight-activated hydraulic knee joint according to claim 12, in which the rotary shaft co-operates with a slot in the side of the piston to effect movement of the piston.

14. A patient-weight-activated hydraulic knee joint according to claim 12, in which the hydraulic valve further comprises a valve seat which may be substantially sealed by the piston to close the second hydraulic line, the area of the piston being much greater than the area of the valve seat.

15. A patient weight-activated hydraulic knee joint according to claim 14, in which the hydraulic valve further comprises a passage leading from the chamber to the hydraulic line and containing a needle valve.

16. A patient-weight-activated hydraulic knee joint according to claim 1, in which the knee attachment comprises a substantially ball-like member.

* * * * *